(12) United States Patent
Dekeyser et al.

(10) Patent No.: US 7,399,757 B1
(45) Date of Patent: Jul. 15, 2008

(54) PESTICIDAL DIAZENE OXIDE CARBOXYLATES

(75) Inventors: Mark A. Dekeyser, Waterloo (CA); Paul T. McDonald, Middlebury, CT (US)

(73) Assignee: Chemtura Corporation, Middlebury, CT (US)

( * ) Notice: Subject to any disclaimer, the term of this patent is extended or adjusted under 35 U.S.C. 154(b) by 0 days.

(21) Appl. No.: 11/804,282

(22) Filed: May 16, 2007

(51) Int. Cl.
C07C 291/08 (2006.01)
A61K 31/655 (2006.01)
(52) U.S. Cl. .................. 514/149; 534/556; 534/566
(58) Field of Classification Search ................ 534/556, 534/566; 514/149
See application file for complete search history.

(56) References Cited

U.S. PATENT DOCUMENTS

| | | | |
|---|---|---|---|
| 5,084,448 A | 1/1992 | Gray et al. | |
| 5,376,679 A | 12/1994 | Pearson et al. | |
| 5,438,123 A * | 8/1995 | Dekeyser et al. | 534/885 |
| 6,093,843 A * | 7/2000 | Chee et al. | 560/27 |
| 6,706,895 B1 * | 3/2004 | Park et al. | 549/75 |

OTHER PUBLICATIONS

Dekeyser et al., Journal of Agricultural and Food Chemistry, 4396), 1705-1707, 1995.*
Mortarini et al., "Antifungal Activity of Methyl and Ethyl Phenyldiazenecarboxylate 2-Oxide Derivatives" appearing in European *Journal of Medicinal Chemistry* at pp. 475-478 (1980).

* cited by examiner

*Primary Examiner*—Fiona T Powers
(74) *Attorney, Agent, or Firm*—Daniel Reitenbach

(57) ABSTRACT

Pesticidal compounds having the structural formula

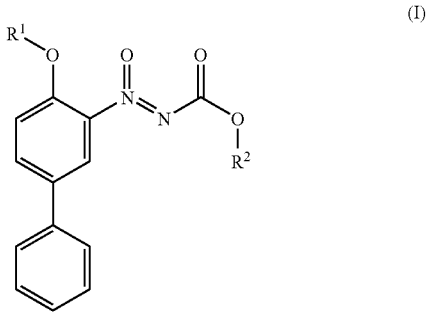

(I)

wherein $R^1$ and $R^2$ are each, independently, $C_{1-6}$ alkyl, compositions comprising the compounds and methods for their use as pesticides.

10 Claims, No Drawings

PESTICIDAL DIAZENE OXIDE CARBOXYLATES

FIELD OF THE INVENTION

The present invention relates to certain diazene oxide carboxylate compounds and compositions, that are useful as pesticides. The present invention also relates to a method for controlling pests such as mites, by contacting the pests with a pesticidally effective amount of the diazene oxide carboxylate compounds, or by applying the diazene oxide carboxylate compounds to plant foliage susceptible to attack by said pests.

BACKGROUND OF THE INVENTION

U.S. Pat. No. 5,438,123 describes certain pesticidal phenylhydrazine derivatives of the formulas:

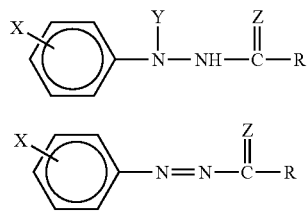

wherein:

X is a) phenyl; lower phenylalkoxy; phenoxy; or benzyl; or b) one substituent from group a) and one or more substituents selected from $C_1$-$C_4$ alkoxy; halogen; lower alkyl; and lower alkylthio; or c) along with the phenyl to which it is attached, forms a multiple fused ring heterocycle such as dibenzofuranyl;

Y is H, $C_1$-$C_4$ alkanoyl, $C_1$-$C_4$ haloalkanoyl, dialkoxyphosphoryl, alkylaminocarbonyl, haloalkylsulfonyl, or $C_1$-$C_4$ alkoxy carbonyl; and R is H, $C_1$-$C_6$ alkyl, $C_1$-$C_6$ alkoxy, $C_3$-$C_6$ cycloalkoxy, haloalkyl, alkoxyalkyl, arylalkoxy, alkenyl, alkylthio, alkoxycarbonyl, alkylamino, heteroaryl, arylalkyl, haloalkoxy, aryloxy, or $C_3$-$C_6$ cycloalkyl; and Z is O or S.

U.S. Pat. No. 5,376,679 discloses a method of combating a fungus, and/or yeast, and/or bacterium, and/or nematode, which method comprises treating plants subject to attack with a compound of the formula:

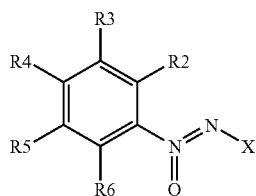

wherein R2 and R3 together, or R3 and R4 together, represent a $C_{34}$ oxyalkylene or oxyalkylene chain optionally substituted by 1-2 $C_{1-6}$ alkyl, $C_{1-6}$ haloalkyl, $C_{1-6}$ hydroxyalkyl, $C_{1-6}$ alkoxyalkyl or phenyl groups, or by one alkylene group —(CH$_2$)$_4$-across adjacent carbon atoms, or by a group =O; the ring is optionally-substituted at any or each of the remaining sites R5, R6 and R2 or R4, wherein each of R5, R6 and R2 or R4 independently represent a halogen atom or a $C_{1-6}$ alkyl or $C_{1-6}$ alkoxycarbonyl group; and X represents a cyano group.

U.S. Pat. No. 5,084,448 discloses a method of combating a fungus, which method comprises treating the fungus with a fungicidally effective amount of a compound of the formula:

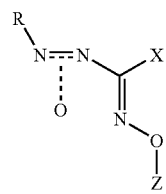

wherein R represents an optionally substituted aryl group; X represents a hydrogen atom or an amino group or an optionally substituted alkyl, aryl, or thienyl group, and Z represents a hydrogen atom or alkanoyl group.

Mortarini, V. et al. (*European Journal of Medicinal Chemistry*, pp. 475-478 (1980)) disclose antifungal activity of methyl and ethyl phenyldiazenecarboxylate 2-oxide derivatives. The phenyl group was optionally substituted by halogen, nitro, alkoxy, or alkyl.

It is an object of this invention to provide novel diazene oxide carboxylate compounds and compositions.

It is a further object of this invention to provide a method for controlling pests using the diazene oxide carboxylate compounds and compositions.

SUMMARY OF THE INVENTION

The present invention relates to diazene oxide carboxylate compounds of the structural formula:

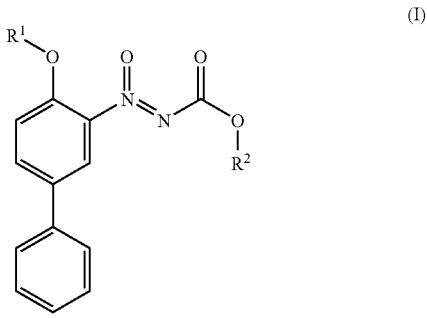

wherein $R^1$ and $R^2$ are each, independently, $C_{1-6}$ alkyl.

The present invention is also directed to a method for controlling pests such as mites by contacting the pests with a pesticidally effective amount of at least one diazene oxide carboxylate compound of the structural formula:

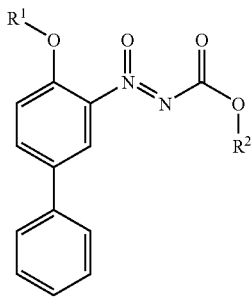

(I)

wherein $R^1$ and $R^2$ are each, independently, $C_{1-6}$ alkyl.

In still another aspect, the present invention is directed to a composition comprising:

(A) a pesticidally effective amount of a diazene oxide carboxylate compound of the structural formula:

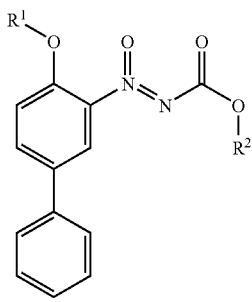

(I)

wherein $R^1$ and $R^2$ are each, independently, $C_{1-6}$ alkyl; and
(B) a suitable carrier.

DETAILED DESCRIPTION OF THE INVENTION

The present invention is directed to diazene oxide carboxylate compounds of the structural formula:

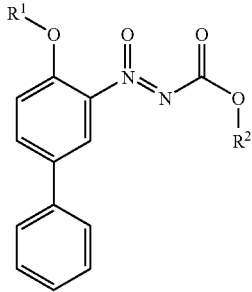

(I)

wherein $R^1$ and $R^2$ are each, independently, $C_{1-6}$ alkyl, use of the diazene oxide carboxylate compounds as pesticides, e.g., insecticides, acaricides, and nematicides, and compositions comprising the diazene oxide carboxylate compounds. Preferably, $R^1$ and $R^2$ are each, independently, methyl, ethyl, propyl, isopropyl, butyl, sec-butyl, isobutyl, tert-butyl, pentyl, isopentyl, hexyl, or isohexyl. More preferably, $R^1$ and $R^2$ are each, independently, lower alkyl of from one to four carbon atoms. Most preferably, $R^1$ is methyl or ethyl, and $R^2$ is methyl, ethyl, or isopropyl.

The diazene oxide carboxylate compounds are preferably useful as acaricides for the control of mites and other acarids.

The compounds of the present invention can be prepared by reacting a suitably substituted diazene carboxylate compound of the formula II:

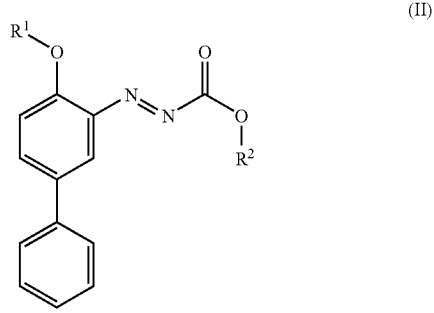

(II)

wherein $R^1$ and $R^2$ are each, independently, $C_{1-6}$ alkyl, with an oxidizing agent, such as meta-chloroperbenzoic acid or other "peroxy" reagent, in a suitable inert organic solvent, for example a halogenated hydrocarbon, such as dichloromethane, at a temperature in the range, suitably, −20° to 60° C. Compounds of the formula (I) are known and may be prepared by methods described in U.S. Pat. No. 5,438,123, the disclosure of which is incorporated herein by reference in its entirety.

The compositions of this invention comprise (a) a compound having a structure within that of formula I above, and (b) a suitable carrier. Such suitable carriers may be solid or liquid in nature. The compositions are preferably pesticidally active and more preferably, acaricidally active.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of the resulting pesticide composition.

The pesticidal compositions may alternatively comprise solid carriers taking the form of dusts, granules, wettable powders, pastes, aerosols, emulsions, emulsifiable concentrates, and water-soluble solids.

For example, the pesticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation or seed treatment, are suitably prepared using a granular or pellitized form of carrier such as granular clays, vermiculite, charcoal or corn cobs.

Alternatively, the pesticidal compounds may be applied in liquids or sprays when utilized in a liquid carrier, such as in a solution comprising a compatible solvent such as acetone, benzene, toluene or kerosene, or as dispersed in a suitable non-solvent medium, for example, water.

Another method of application to loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combated, as well as upon the specific chemical composition and formulation of the compound being employed, the method of applying the compound/formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice and the like.

To combat pests, sprays of the compounds may be applied to the pests directly and/or to plants upon which they feed or nest. The pesticidally active formulations may also be applied to the soil or other medium in which the pests are present.

Harmful insects, nematodes and mites attack a wide variety of plants, including both ornamental and agricultural plants and inflict damage by consuming roots and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will, of course, vary depending upon such circumstances as geographic area, climate, topography, plant tolerance, etc. For specific circumstances, one skilled in the art may readily determine the proper compound, concentration and method of application by routine experimentation.

The compounds and compositions of this invention are particularly useful as acaricides for foliar application.

EXAMPLES

The following examples are presented to illustrate the present invention.

Example 1

Preparation of 1-Methylethyl 2-(4-methoxy-[1,1'-biphenyl]-3-yl)diazenecarboxylate 2-oxide A solution of 1-methylethyl (4-methoxy-[1,1'-biphenyl]-3-yl)diazenecarboxylate (10.25 g) in dichloromethane (160 mL) was cooled in an ice bath and meta-chloroperbenzoic acid (14.8 g) was added in portions with stirring. Additional dichloromethane (90 mL) was added and the solution left to stir at room temperature for 3 days. To the mixture, dichloromethane (200 mL) was added and washed with saturated potassium bicarbonate (300 mL), followed by saturated sodium sulfite (2×200 mL) and finally saturated potassium bicarbonate (200 mL). The organic phase was dried with sodium sulfate and evaporated to give the product as a brown-orange solid (9.78 g). The product was purified using silica gel chromatography (1:5 ethyl acetate:hexane). Evaporation of the desired fractions gave purified product as an orange solid (6.19 g), with melting point 102-106° C. The product was analyzed by NMR (CDCl$_3$) which showed 1.4 d (6H), 3.9 s (3H), 5.2 m (1H), 7.1-7.9 m (8H), where d signifies doublet, s signifies singlet, and m signifies multiplet; and by LC/MS which showed m/z: 315.8 (M+H)$^+$, (M)$^+$ 314.7.

Example 2

Preparation of Formulations

The remaining examples relate to the pesticidal use of compounds of this invention. In all these examples a stock solution for the compounds was prepared at 3000 ppm by dissolving 0.3 grams of the compound to be tested in 10 mL of acetone and adding 90 mL of distilled water plus four drops of ethoxylated sorbitan monolaurate, or a similar suitable wetting agent. For each example that follows, this stock solution was used and the specified dilutions made. All the tests discussed below, which involved treatment with compounds of this invention, were always repeated with controls, in which the active compound was not provided, to permit a comparison upon which the percent control was calculated.

Example 3

Mite Adulticide and Mite Ovicide/Larvicide Tests

One day before treatment, a "FIG. 8" configuration of tree tanglefoot was applied to each of two cowpea primary leaves, one from each of two plants in a pot. In each figure, the circle nearer the stem was designated for the mite ovicide/larvicide test and the circle further from the stem was designated for the mite adulticide test.

Groups of adult mites (*Tetranychus urticae* Koch) were transferred into ovicide circles one day before treatment and the females were allowed to deposit eggs until one hour before treatment when they were removed. Plants were sprayed to run off with a 1000 ppm solution diluted from the 3000 ppm stock solution.

One day following treatment, groups of approximately 25 adult mites were transferred into the adulticide circles. Five days later these circles were examined for live mites remaining on the leaves. The percent control was estimated based on the number of mites surviving on the check plants.

Nine days following treatment, the ovicide/larvicide circles were examined for hatched eggs and living immature mites. The percent control was estimated based on the number of eggs hatching and immature mites surviving on the check plants. When the treatment effect was to eggs, control was designated as ovicidal (O); when the treatment effect was to immatures, control was designated as larvicidal (L).

Results of the mite adulticide (MI) and ovicide/larvicide (MIOVL) tests on Compound 1 are as follows: MI 100% Control, MIOVL (L) 100% Control.

What is claimed is:

1. A compound having the structural formula:

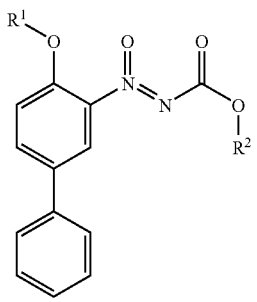

(I)

wherein $R^1$ and $R^2$ are each, independently, $C_{1-6}$ alkyl.

2. A compound in accordance with claim 1 wherein $R^1$ and $R^2$ are each, independently, methyl, ethyl, propyl, isopropyl, butyl, sec-butyl, isobutyl, tert-butyl, pentyl, isopentyl, hexyl, or isohexyl.

3. A compound in accordance with claim 1 wherein $R^1$ and $R^2$ are each, independently, CIA alkyl.

4. A compound in accordance with claim 3 wherein $R^1$ is methyl or ethyl, and $R^2$ is methyl, ethyl, or isopropyl.

5. A pesticidal composition comprising:
   A) a pesticidally effective amount of a compound in accordance with claim 1; and
   B) an acceptable carrier.

6. A pesticidal composition comprising:
   A) a pesticidally effective amount of a compound in accordance with claim 2; and
   B) an acceptable carrier.

7. A pesticidal composition comprising:
   A) a pesticidally effective amount of a compound in accordance with claim 3; and
   B) an acceptable carrier.

8. A pesticidal composition comprising:
   A) a pesticidally effective amount of a compound in accordance with claim 4; and
   B) an acceptable carrier.

9. A process for controlling undesirable pests which comprises applying to a locus to be protected a pesticidally effective amount of a compound in accordance with claim 1.

10. A process for controlling undesirable pests which comprises applying to a locus to be protected a pesticidally effective amount of a composition in accordance with claim 5.

* * * * *